United States Patent
Hirayama et al.

(10) Patent No.: US 8,822,958 B2
(45) Date of Patent: Sep. 2, 2014

(54) RADIATION TREATMENT PLANNING SYSTEM

(71) Applicant: Hitachi, Ltd., Tokyo (JP)

(72) Inventors: Shusuke Hirayama, Hitachinaka (JP); Rintaro Fujimoto, Hitachinaka (JP); Yoshihiko Nagamine, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 13/958,716

(22) Filed: Aug. 5, 2013

(65) Prior Publication Data

US 2014/0073831 A1  Mar. 13, 2014

(30) Foreign Application Priority Data

Sep. 12, 2012  (JP) ................. 2012-200193

(51) Int. Cl.
- *G21K 5/00* (2006.01)
- *A61N 5/01* (2006.01)
- *A61N 5/06* (2006.01)
- *A61N 5/10* (2006.01)

(52) U.S. Cl.
CPC .. *A61N 5/01* (2013.01); *G21K 5/00* (2013.01); *A61N 2005/0635* (2013.01); *A61N 2005/0627* (2013.01); *A61N 2005/1072* (2013.01)
USPC .......................... 250/492.1; 250/492.3; 600/1

(58) Field of Classification Search
CPC ............. G21K 5/00; G21K 5/04; G21K 5/08; G21K 5/10; A61N 2005/00; A61N 2005/0626; A61N 2005/0627; A61N 2005/0635; A61N 2005/0642; A61N 2005/10; A61N 2005/103; A61N 2005/1071; A61N 2005/1072; A61N 5/01

See application file for complete search history.

(56) References Cited

U.S. PATENT DOCUMENTS

| | | | | |
|---|---|---|---|---|
| 6,049,587 | A * | 4/2000 | Leksell et al. | 378/65 |
| 2007/0286343 | A1* | 12/2007 | Maciunas et al. | 378/65 |

FOREIGN PATENT DOCUMENTS

| | | |
|---|---|---|
| EP | 2 602 004 A2 | 6/2013 |
| JP | 2002-263208 A | 9/2002 |
| WO | 03/092789 A2 | 11/2003 |
| WO | 2007/126782 A2 | 11/2007 |

OTHER PUBLICATIONS

A Lomax; "Intensity modulation methods for proton radiotherapy"; Phys. Med. Biol.; 44 (1999); 185-205.

(Continued)

*Primary Examiner* — Nicole Ippolito
(74) *Attorney, Agent, or Firm* — Mattingly & Malur, PC (57) ABSTRACT

Optimal irradiation conditions determined by iterative calculation are based upon an operator-defined irradiating direction, prescription dose, and other conditions. Dose matrixes A and B relating doses to calculation points from a beam delivered to irradiating positions are divided into a dose matrix $A_M$ or $B_M$ for the calculation points in a target region that are present at distances equal to or less than a distance L from the beam axis of the beam delivered to each spot, and a dose matrix $A_S$ or $B_S$ for the calculation points that are present at distances greater than L. When the iterative calculation is conducted following completion of the division, dose values and $\vec{d}_S^{(1)}$ and $\vec{d}_S^{(2)}$ that include the dose matrixes $A_S$ and $B_S$ are regarded as constants, and if updating conditions are satisfied, an objective function is recalculated using the values of the dose matrixes A, B and the spot irradiation dose $\vec{x}$.

6 Claims, 7 Drawing Sheets

(56) References Cited

OTHER PUBLICATIONS

Pedroni et al.; "Experimental characterization and physical modelling of the dose distribution of scanned proton pencil beams"; Phys. Med. Biol.; 50 (2005); 541-561.

Li et al.; "An efficient dose calculation strategy for intensity modulated proton therapy"; Phys. Med. Biol.; 56 (2011); N71.

European Search Report received in European Application No. 13179413 dated Jan. 31, 2014.

* cited by examiner

RADIATION TREATMENT PLANNING SYSTEM

BACKGROUND OF THE INVENTION

The present invention relates to a radiation treatment planning system.

In radiation therapy, a treatment for target tumor cells is administered by irradiating the cells with radiation. While X-rays are most commonly used in radiation-based treatments, the therapy that uses charged particle beams represented by particle beams highly dose-convergent upon targets (i.e., proton beams and carbon beams) is increasing in demand.

In radiation therapy, excess or deficiency of irradiation dose is likely to lead to side effects upon non-tumor normal tissues or to tumor recurrence. It is also demanded in particle therapy that a tumor region be irradiated with a dose that has been specified so that beam concentrates upon the tumor region as accurately as possible and as much as possible.

The use of scanning in particle therapy is increasing as a method of concentrating a dose. The scanning method is intended to bend a thin beam of particles via two sets of scanning magnets, guide the particle beam to any position within a plane, and thereby irradiate the inside of a tumor as if it were completely coated with the particles, to impart a higher dose to the tumor region only.

The scanning method has an advantage of there basically being no need of the patient-specific device, such as a collimator, that is used in a scattering irradiation method to form a distribution into the tumor shape. The scanning method also has an advantage in that various distributions can be formed easily.

To implement the scanning method, it becomes a vital step to draw up a plan with a radiation treatment planning system before starting actual irradiation. The radiation treatment planning system simulates the dose distribution within the patient's body by conducting numerical calculations based upon his/her in-vivo information obtained from CT images and the like. An operator, while referring to the calculation results supplied from the radiation treatment planning system, determines a particle beam irradiation direction, beam energy, an irradiating position, an irradiation dose, and other irradiation conditions.

The following briefly describes a general process employed for the simulation.

The operator first enters a target region to be irradiated with radiation. The target region is mainly entered onto slices of a CT image. The entered data is registered in the radiation treatment planning system by the operator and saved on a memory of this system as three-dimensional image data. If necessary, a position of a organ at risk whose exposure to the radiation is to be minimized is likewise entered and registered.

Next, the operator sets a prescription dose that is delivered in the target region, for each registered region on the slices. This setting operation is performed for the previously registered target region and organ at risk. For the target region, for example, a dose sufficient for necrosing the tumor is specified. Maximum and minimum values of the dose to be delivered to the target region are specified in most cases. For the organ at risk, on the other hand, a permissible dose is set as a maximum dose at which the organ is considered to be able to withstand the irradiation. If a plurality of target regions or organ at risks are present, relative importance of each can also be set as a weight.

Following the above, a determination is conducted of the irradiation conditions for achieving the dose distribution that satisfies the prescription dose. Until the dose distribution deemed appropriate has been obtained, the operator adjusts parameters relating to the irradiation conditions to be determined using the radiation treatment planning system. Widely adopted to set these parameters efficiently are methods using an objective function that represents a digitized deviation from the prescription dose, as described in JP-2002-263208-A, Non-Patent Document 1 (A Lomax, "Intensity modulation methods for proton radiotherapy", Phys. Med. Biol., 44 (1999), 185-205) and Non-Patent Document 2 (Pedroni et al., "Experimental characterization and physical modeling of the dose distribution of scanned proton pencil beams", Phys. Med. Biol., 50 (2005), 541-561), for example. The objective function is defined to become smaller the more the dose distribution fulfills the prescription dose. Calculations are repeated to search for the irradiation dose having the smallest value of the objective function, whereby an optimum irradiation dose is obtained.

Examples of a parameter determined by the objective function include an irradiation dose to various spots in particle beam scanning irradiation (this dose is hereinafter referred to as the spot irradiation dose). An example of a parameter search method using the objective function is the method of searching for the spot irradiation dose, proposed in Non-Patent Document 1. In this search method, doses to be imparted to calculation points within the target region or organ at risk are expressed in terms of dose matrix as the doses from the beams which have been delivered to each spot, and the objective function is calculated from the dose matrix with each search for the spot irradiation dose.

It is also known that as described in Non-Patent Document 2, scanning irradiation methods increase the beam size because of the influence of nuclear reactions in water or scattering inside the irradiation system.

SUMMARY OF THE INVENTION

As discussed above, the spot irradiation dose search method, proposed in Non-Patent Document 1, requires calculating the objective function from the dose matrix with each search for the spot irradiation dose. In the scanning irradiation methods, on the other hand, the beam size increases because of the influence of the nuclear reactions in water or scattering inside the irradiation system (source: Non-Patent Document 2). The increase in the beam size accordingly increases non-zero elements in the dose matrix used for the irradiation dose search, thus causes an increase in the load of iterative calculation and hence in a significant increase in calculation time.

An object of the present invention is to provide a radiation treatment planning system that reduces a time needed to determine, by iterative calculation, optimal irradiation conditions based upon an operator-defined irradiating direction, prescription dose, and other conditions.

In order to achieve the above object, an aspect of the present invention is a radiation treatment planning system configured to draw up a treatment plan for conducting a treatment that involves irradiation with radiation, the system comprising: an entry device for an operator to enter position information about a specific region for which the irradiation with radiation is to be controlled, irradiation conditions predefined by the operator, and other necessary information; a storage device for storing the position information about the specific region, the operator-predefined irradiation conditions, and the other necessary information, each of which has been entered from the entry device; and a calculation unit that sets an objective function based upon the position information and the operator-predefined irradiation conditions stored within the storage device, the calculation unit executing iterative calculation with respect to the objective function to calculate an irradiation parameter having the smallest value of the objective function; wherein the calculation unit is operated to: set a plurality of irradiating positions and a plurality of calculation points within the specific region; set the objective function by dividing a contribution concerning a dose given to the plurality of calculation points by a beam delivered to each irradiating position into a plurality of components, at least including a beam axis proximal component and a beam axis distant component, in accordance with respective distances between a beam axis of the beam delivered to each irradiation position and the plurality of calculation points; and compute the objective function by, during the iterative calculation, regarding the beam axis distant component included in the plurality of components as a constant, and recalculating, only if previously set updating conditions are determined to be satisfied, the dose to be given to the calculation points, inclusive of the beam axis distant component, by use of an irradiation parameter available upon the determination.

The present invention enables reduction in the time needed to determine the optimal irradiation conditions by the iterative calculation based upon the operator-defined irradiating direction, prescription dose, and other conditions.

DESCRIPTION OF THE PREFERRED EMBODIMENT

An embodiment of a radiation treatment planning system according to the present invention will be described hereunder using the accompanying drawings.

The embodiment of the radiation treatment planning system according to the present invention is described below using FIGS. 1 to 7.

Figure 1:
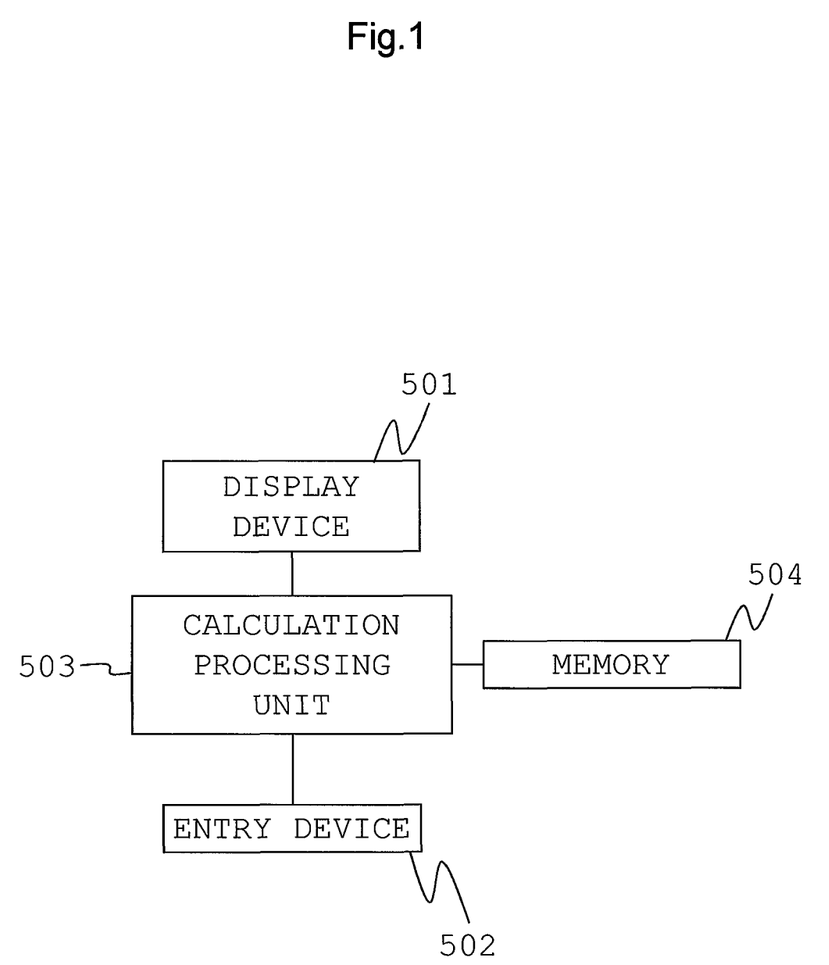
FIG. 1 is a diagram showing schematically a configuration of a radiation treatment planning system according to an embodiment of the present invention.

FIG. 1 is a diagram showing schematically a configuration of the radiation treatment planning system according to the embodiment of the present invention.

Referring to FIG. 1, the radiation treatment planning system according to the present embodiment schematically includes a display device 501, an entry device 502, an calculation processing unit 503, and a memory (storage device) 504.

The display device 501 has a region entry screen, on which CT images and other medical image information (tomographic image information) obtained by imaging a patient's target volume are displayed on a slice-by-slice basis. The image information is stored within, for example, the memory 504 of the radiation treatment planning system. The entry device 502 is, for example, a keyboard and/or a mouse.

The following first describes details of setting up a treatment plan for particle therapy in a scanning irradiation method, the treatment plan setup being done using the radiation treatment planning system according to the present embodiment.

Figure 2:
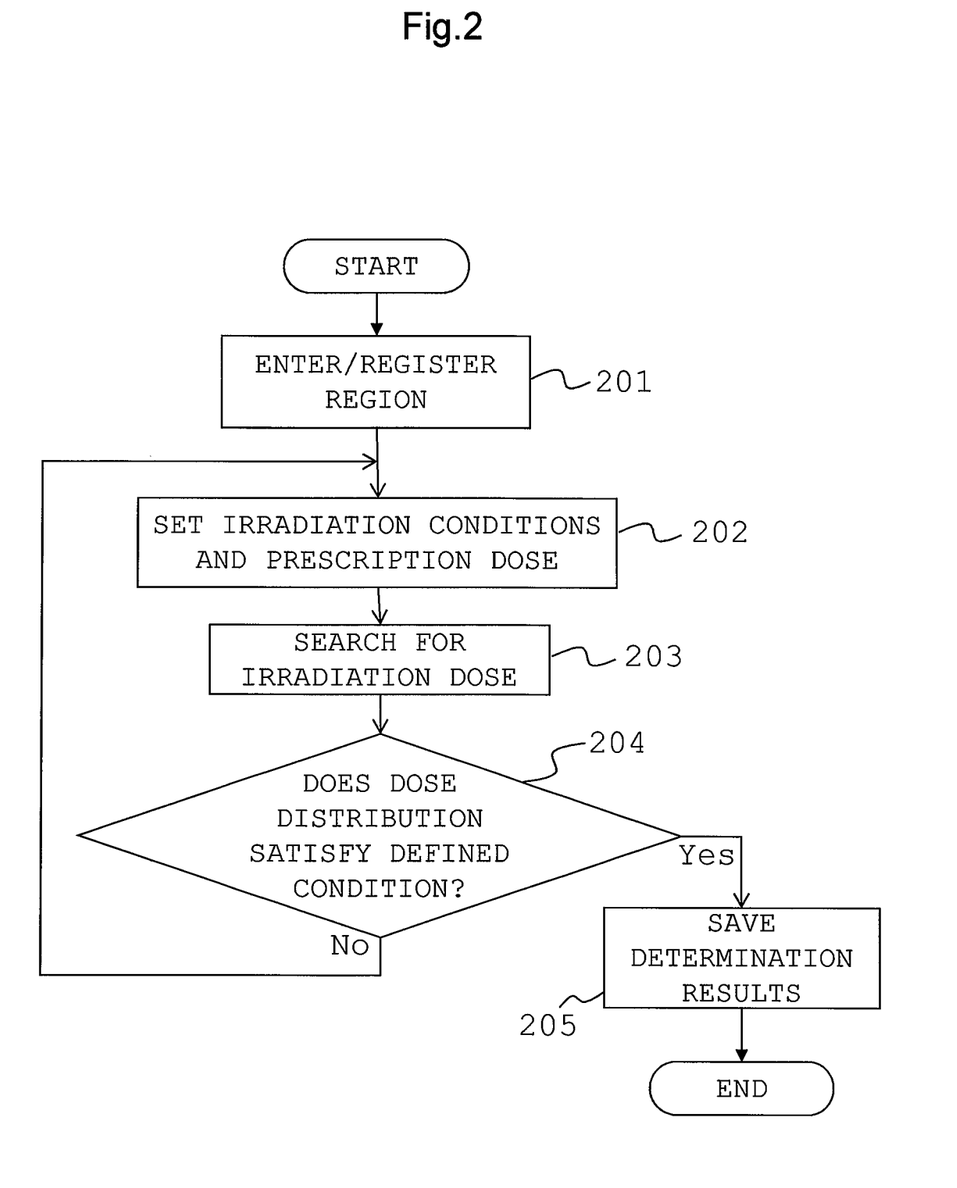
FIG. 2 is a flowchart showing a flow of treatment plan setup using the radiation treatment planning system according to the embodiment of the present invention.
Figure 3:
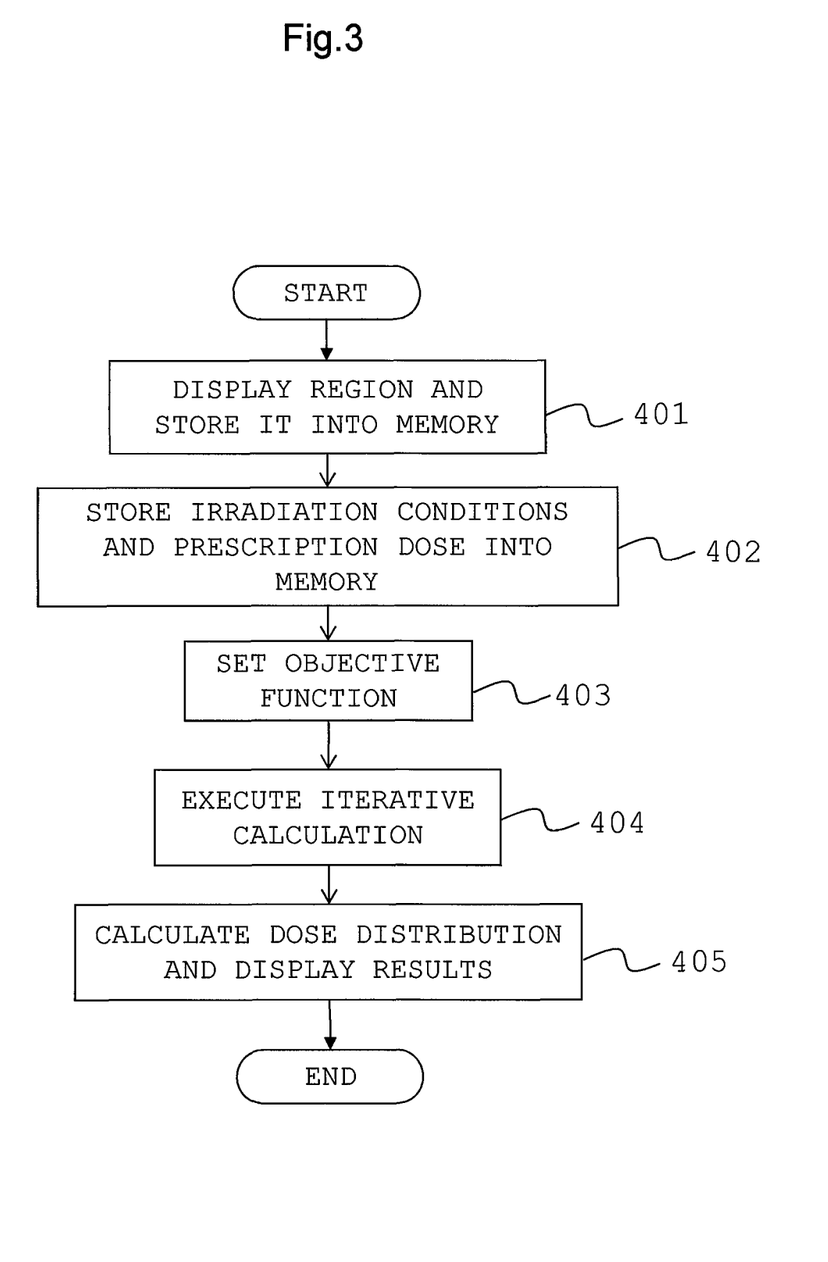
FIG. 3 is a flowchart of processing functions which the radiation treatment planning system according to the embodiment of the present invention performs in setting up a treatment plan.

FIG. 2 is a flowchart showing a flow of the treatment plan setup using the radiation treatment planning system according to the embodiment of the present invention, and FIG. 3 is a flowchart of processing functions which the radiation treatment planning system according to the embodiment of the present invention performs during treatment planning.

To begin with, an operator uses the entry device 502, such as a mouse, to enter the region to be specified for each slice of the CT image, on the region entry screen of the display device 501. At this time, if the organ at risk whose exposure to the radiation is to be minimized is present near the target region or if any other regions that require assessment and/or control are present, the operator also enters positions of these regions, as of the organ at risk, in a manner similar to the above, using the entry device 502 (step 201 in FIG. 2).

After the entry for each slice, the operator gives an instruction for registering the entered regions 601 and 602 in the radiation treatment planning system (FIG. 2, step 201). This results in the operator-entered regions being saved in the memory 504 of the radiation treatment planning system as three-dimensional position information (FIG. 2, step 401).

Figure 4:
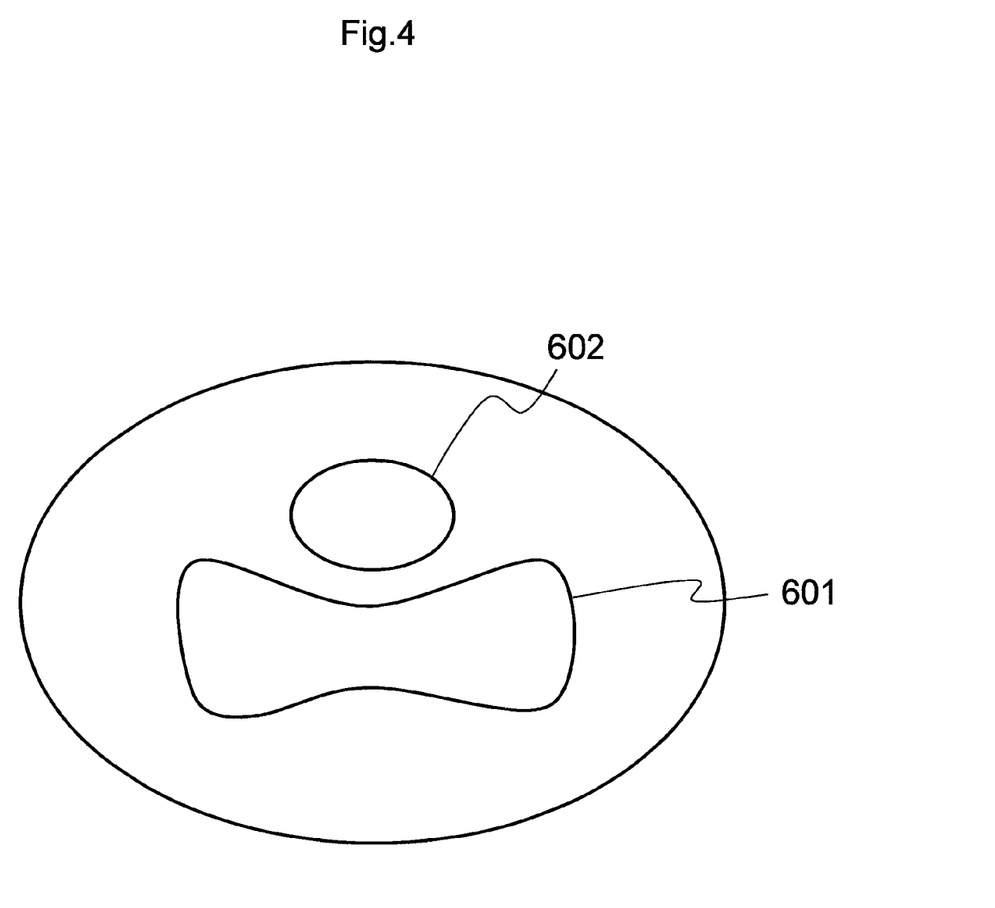
FIG. 4 is a diagram showing a state in which an operator has entered a target region and a organ at risk on a slice of a CT image using a region entry screen of a display device in the radiation treatment planning system according to the embodiment of the present invention, and registered the entered target region and organ at risk.

FIG. 4 is a diagram showing a state in which the operator has entered and registered the target region and organ at risk on a slice of the CT image displayed on the region entry screen of the display device 501, the target region being shown as 601 and the organ at risk as 602.

After the above, the operator determines and enters the irradiation conditions with respect to the registered target region 601 and organ at risk 602 (FIG. 2, step 202). That is to say, an irradiation port quantity and irradiation directions are determined on the basis of the positions of the target region 601 and organ at risk 602. Not all of the irradiation conditions may be determined by the operator; the radiation treatment planning system may determine a part of them automatically.

As in the present embodiment, when a scanning irradiation method is adopted in particle therapy, a number of beam irradiating positions need to be defined and beam energy and irradiation time intervals for each irradiating position can also be data items to be set. In line with the operator-entered irradiation conditions, the radiation treatment planning system sets the irradiating positions, the energy, the irradiation time intervals, and other irradiation parameter data, and saves the data settings in the memory 504.

In addition to the above, the operator defines the prescription doses to the registered regions 601, 602. For the target region, maximum and minimum values of the prescription dose to be applied to the region are often entered, but in the present embodiment, one value is specified as the dose to be delivered to the target region 601. For the organ at risk, however, a permissible dose is often set. In the present embodiment, a permissible dose value is specified for the organ at risk 602.

The thus-set irradiation directions and prescription doses are saved in the memory 504 of the radiation treatment planning system (FIG. 3, step 402). The radiation treatment planning system usually defines the objective function that is a digitized deviation from the prescription dose (FIG. 3, step 403), and minimizes the defined objective function by iterative calculations to compute the parameter left over after the minimization (FIG. 3, step 404).

As in the present embodiment, when a scanning irradiation method is adopted in particle therapy, an example of a parameter calculated using an objective function is the irradiation dose to each spot (hereinafter, this dose is referred to as the spot irradiation dose).

Figure 7:
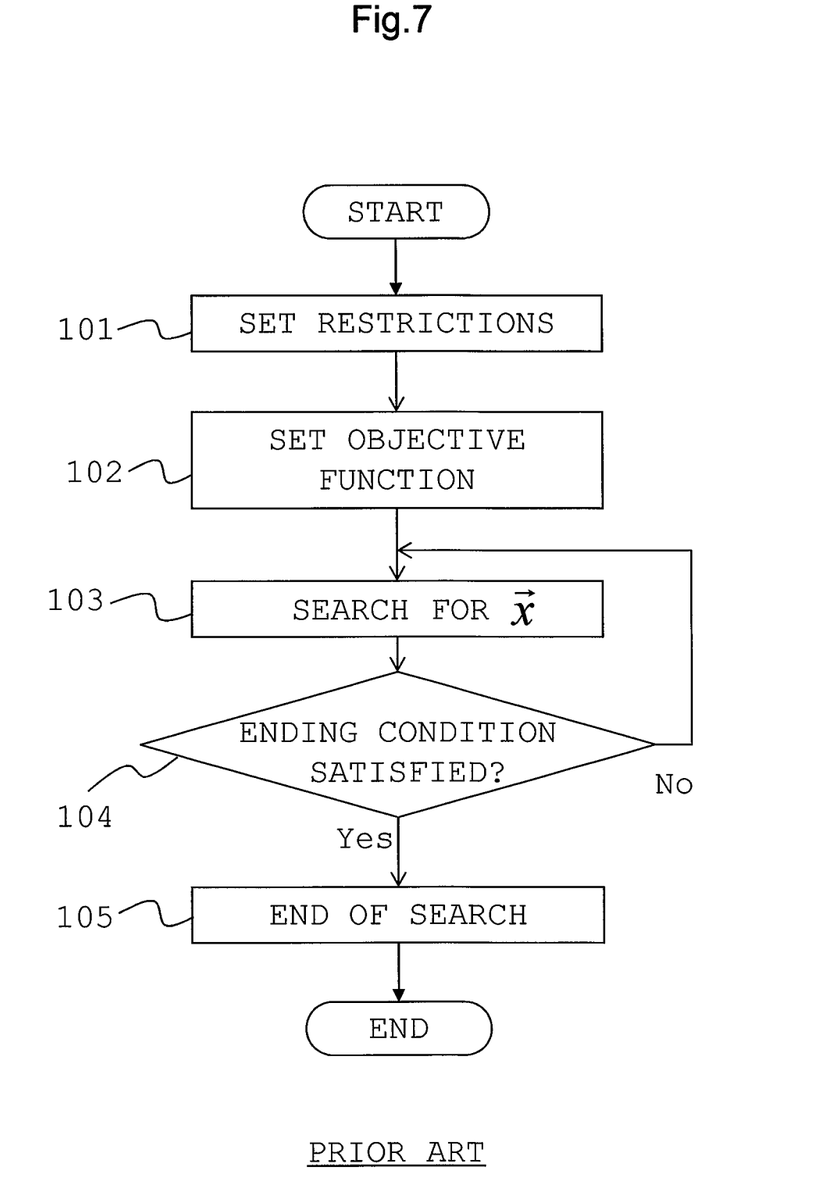
FIG. 7 is a flowchart showing a specific example of processing functions which the radiation treatment planning system according to the embodiment of the conventional invention performs in setting up a treatment plan.

Traditionally, the spot irradiation dose search method as described in Non-Patent Document 1 has been used to determine the spot irradiation dose. FIG. 7 is a flowchart showing a conventional method of a spot irradiation dose search using an objective function. The conventional search method is described below FIG. 7.

First, restrictions are set from the operator-set prescription doses and organ at risk information (FIG. 7, step 101). Next, the radiation treatment planning system sets an "m" number of points and an "n" number of points as dose calculation points, in the target region and the organ at risk, respectively, and creates an objective function based upon the restrictions (FIG. 7, step 102). In this case, if a vector taking for its element the dose values at the "m" number of calculation points within the target region is expressed as $\vec{d}^{(1)}$, a relationship between $\vec{d}^{(1)}$ and a vector $\vec{x}$ taking the spot irradiation dose as its element, is represented by following expression (1):

$$\vec{d}^{(1)} = A\vec{x} \qquad (1)$$

Similarly, if a vector taking for its element the dose values at the "n" number of calculation points within the organ at risk is expressed as $\vec{d}^{(2)}$, a relationship between $\vec{d}^{(2)}$ and $\vec{x}$ is represented by following expression (2):

$$\vec{d}^{(2)} = B\vec{x} \qquad (2)$$

Matrix A is a contribution relating to the doses imparted to each calculation point in the target region from the beams delivered to each spot (hereinafter, this contribution is referred to as a dose matrix). The dose matrix A is calculated from the irradiation directions and the internal information relating to the patient's body, this internal information being based upon the CT image. Matrix B is a contribution relating to the doses imparted to each calculation point in the organ at risk from the beams delivered to each spot (hereinafter, this contribution is likewise referred to as a dose matrix). The dose matrix B is also calculated from the irradiation directions and the internal information.

If the beam applied is too small in beam size (a size of the beam on a surface perpendicular to a traveling direction of the beam), the dose cannot be imparted to any calculation points distant from the beam axis of the beam delivered to the spot. This increases zero-elements of the dose matrix. Conversely if the beam size is too large, the beam applied will have too wider a dose-imparting region, which increases non-zero-elements of the dose matrix.

If a desired dose value "p" and a permissible dose value "l" are set as restrictions for the "m" number of points in the target region and for the "n" number of points in the organ at risk, then the objective function $F(\vec{x})$ is defined as in following expression (3):

$$F(\vec{x}) = \sum_{i=1}^{m} w_i^{(1)}(d_i^{(1)} - p)^2 + \sum_{i=1}^{n} w_i^{(2)}(d_i^{(2)} - l)^2 \theta(d_i^{(2)} - l) \qquad (3)$$

Where $w_i^{(1)}$ and $w_i^{(2)}$ are weights corresponding to the respective points, and these values are entered with the prescription dose by the operator. The first term corresponds to the target region, and $F(\vec{x})$ is smaller as the dose values at the "m" number of points are closer to the prescription dose value "p" that has been set as the desired value. The second term, which relates to the organ at risk, can use any dose value that does not exceed the permissible dose value "l". In addition, $\theta(\vec{d}i^{(2)} - l)$ is a step function, which, if $\vec{d}i^{(2)} < l$, takes a value of 0; otherwise, the step function takes a value of 1.

In conventional radiation treatment planning systems, after the objective function as shown in expression (3) has been generated, iterative calculation is repeated until an ending condition of the iterative calculation has been satisfied. Thus, $\vec{x}$ that minimizes $F(\vec{x})$ is searched for (FIG. 7, steps 103, 104, 105).

The iterative calculation therefore has a problem in that since an increase in the beam size also increases non-zero elements in the dose matrixes A, B, the amount of iterative calculation increases and hence a significant increase in calculation time results.

Figure 5:
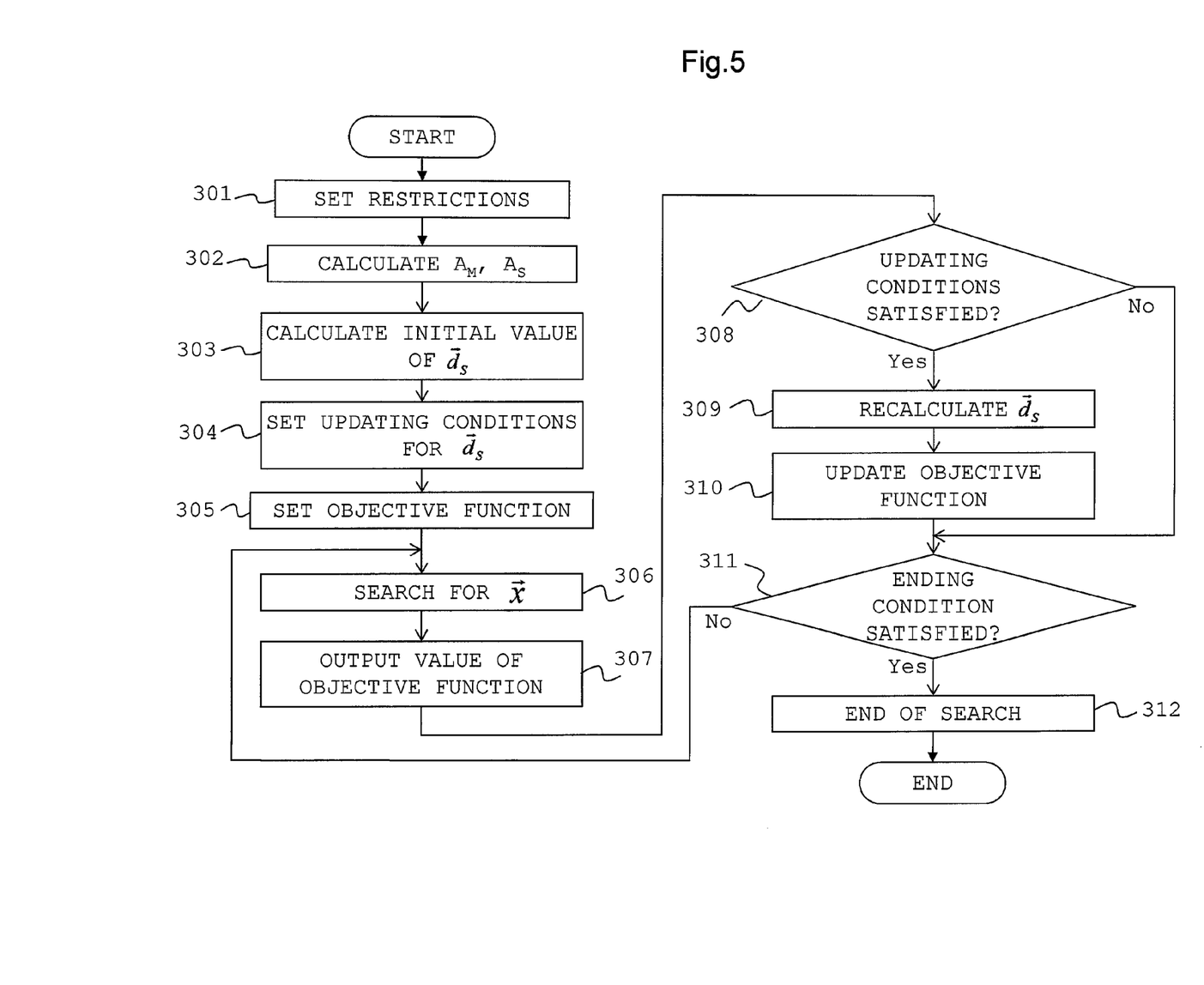
FIG. 5 is a flowchart showing a specific example of processing functions which the radiation treatment planning system according to the embodiment of the present invention performs in setting up a treatment plan.

In contract to the conventional method of searching for the spot irradiation dose, the present embodiment employs the following search method to reduce the calculation time required. FIG. 5 is a flowchart showing the method of searching for the spot irradiation dose in the present embodiment. The spot irradiation dose search method in the present embodiment is described below using FIG. 5.

First, the radiation treatment planning system sets up restrictions from the operator-entered prescription doses and organ at risk information (FIG. 5, step 301).

Next, the radiation treatment planning system sets an "m" number of and an "n" number of dose calculation points in the target region and the organ at risk, respectively, and creates an objective function. The objective function is set as in above expression (3). The following describes how the dose matrixes included in $\vec{d}^{(1)}$, $\vec{d}^{(2)}$ of expression (3) are expressed to generate the objective function in the present invention.

In the present invention, as one of its features and characteristics, the dose matrixes A, B are each divided into a beam axis proximal component and a beam axis distant component in accordance with respective distances between a beam axis of the beam delivered to each spot, and the calculation points. A method of the division affects a convergence result of the objective function. Details of the dividing method will be described later herein. A basis for the division, that is, the distance from the beam axis is set as L in the description of the spot irradiation dose search method according to the present invention.

When the radiation treatment planning system starts the dose calculations, the system divides the dose matrix A relating to the target region, into two components (FIG. 5, step 302). One is the beam axis proximal component (dose matrix $A_M$), which is the contribution relating to the doses imparted to the calculation points in the target region that are present at distances equal to or less than the distance L from the beam axis of each beam delivered to the particular spot. The other is the beam axis distant component (dose matrix $A_S$), which is the contribution relating to the doses imparted to the calculation points in the target region that are present at distances greater than L from the beam axis of each beam delivered to the particular spot. In this case, the dose matrix A is represented using the dose matrix $A_M$ and the dose matrix $A_S$, as in following expression (4):

$$A = A_M + A_S \quad (4)$$

This expression assumes that the element of $A_S$ is small enough relative to that of $A_M$.

Additionally the vector whose element is the spot irradiation dose that becomes a parameter of the objective function is written as $\vec{x}$. A dimension of $\vec{x}$ is a total number of spots.

Next if the vector with the dose values at the "m" number of calculation points in the target region is expressed as $\vec{d}^{(1)}$, a relationship of this vector with respect to the spot irradiation dose $\vec{x}$ is represented as in following expression (5):

$$\vec{d}^{(1)} = A\vec{x} = A_M \vec{x} + A_S \vec{x} = \vec{d}_M^{(1)} + \vec{d}_S^{(1)} \quad (5)$$

where $\vec{d}_M^{(1)}$ denotes, among all the dose values imparted to the "m" number of calculation points, only those affected by proximity of these calculation points to the beam axis (the respective distances from the beam axis are equal to or less than L), and $\vec{d}_S^{(1)}$ denotes the dose values affected by distantness of the calculation points from the beam axis (the respective distances from the beam axis are greater than L).

Likewise, when the radiation treatment planning system starts the dose calculations, the system divides the dose matrix B relating to the organ at risk, into the beam axis proximal component $B_M$ and the beam axis distant component dose matrix $B_S$. At this time, the dose matrix B is represented as in following expression (6):

$$B = B_M + B_S \quad (6)$$

Additionally, if the vector whose element is the dose values at the "n" number of calculation points in the organ at risk is taken as $\vec{d}^{(2)}$, this vector is represented as in following expression (7):

$$\vec{d}^{(2)} = B\vec{x} = B_M \vec{x} + B_S \vec{x} = \vec{d}_M^{(2)} + \vec{d}_S^{(2)} \quad (7)$$

where $\vec{d}_M^{(2)}$ denotes, among all the dose values imparted to the "n" number of calculation points, only those affected by proximity of these calculation points to the beam axis, and $\vec{d}_S^{(2)}$ denotes the dose values affected by distantness of the calculation points from the beam axis.

Next, the system calculates initial values of $\vec{d}_S^{(1)}$ and $\vec{d}_S^{(2)}$ from an initial value of the spot irradiation dose $\vec{x}$ and the dose matrix $A_S$ (FIG. 5, step 303).

In addition, the operator predefines updating conditions as conditions for updating $\vec{d}_S^{(1)}$, $\vec{d}_S^{(2)}$, enters the updating conditions from the entry device 502, and sets them in the memory 504 (FIG. 5, step 304).

After that, in step 301 of FIG. 5, when the desired dose value "p" and the permissible dose value "l" are set as restrictions for the "m" number of calculation points in the target region and for the "n" number of calculation points in the organ at risk, respectively, the radiation treatment planning system uses above-calculated $A_M$, $A_S$, $B_M$, $B_S$ to generate the objective function $F(\vec{x})$ as in following expression (8):

$$F(\vec{x}) = \sum_{i=1}^{m} w_i^{(1)} \left( \vec{d}_{M,i}^{(1)} + \vec{d}_{S,i}^{(1)} - p \right)^2 + \sum_{i=1}^{n} w_i^{(2)} \left( \vec{d}_{M,i}^{(2)} + \vec{d}_{S,i}^{(2)} - l \right)^2 \theta\left( \vec{d}_{M,i}^{(2)} + \vec{d}_{S,i}^{(2)} - l \right) \quad (8)$$

As described above, $w_i^{(1)}$ and $w_i^{(2)}$ are the weights corresponding to the respective points, and these values are entered with the prescription dose by the operator. The first term corresponds to the target region, and $F(\vec{x})$ is smaller as the dose values at the "m" number of points are closer to the prescription dose value "p" that was set as the desired value. The second term, which relates to the organ at risk, can use any dose value not exceeding the permissible dose value "l", so if $(\vec{d}_{M,i}^{(2)} + \vec{d}_{S,i}^{(2)})$ is less than l, then $\theta(\vec{d}_{M,i}^{(2)} + \vec{d}_{S,i}^{(2)} - l)$ is 0.

The radiation treatment planning system, after generating the objective function of expression (8) in step 305 of FIG. 5, repeats the iterative calculation process until the ending condition of the iterative calculation has been satisfied. Thus, $\vec{x}$ that minimizes $F(\vec{x})$ is searched for and the particular $\vec{x}$ value is output (FIG. 5, steps 306, 307).

Originally, during the iterative calculation, $\vec{d}^{(1)}$ and $\vec{d}^{(2)}$ need to be updated each time a calculation cycle is executed according to the expression (5) or the expression (7). The radiation treatment planning system of the present embodiment, however, can reduce the calculation time required for updating, by handling $\vec{d}_S^{(1)}$ and $\vec{d}_S^{(2)}$ as constants.

Here, as described above, the initial values of $\vec{d}_S^{(1)}$ and $\vec{d}_S^{(1)}$ are calculated from the initial value of the spot irradiation dose $\vec{x}$ and the dose matrix $A_S$ (FIG. 5, step 303). During subsequent cycles of the iterative calculation, $\vec{d}_S^{(1)}$ and $\vec{d}_S^{(2)}$ are handled as constants.

While the iterative calculation is being continued, a change in spot irradiation dose also causes changes in $\vec{d}_S^{(1)}$ and $\vec{d}_S^{(2)}$. If the execution of the iterative calculation with $\vec{d}_S^{(1)}$ and $\vec{d}_S^{(2)}$ as constants is continued without the $\vec{d}_S^{(1)}$ and $\vec{d}_S^{(2)}$ changes being taken into account, a departure of a computed value of the objective function from that of the objective function as actually calculated without $\vec{d}_S^{(1)}$ and $\vec{d}_S^{(2)}$ not being handled as constants might be gradually significant, rendering it difficult to ensure accuracy of the computed spot irradiation dose $\vec{x}$.

In order to incorporate the changes in $\vec{d}_S^{(1)}$ and $\vec{d}_S^{(2)}$, the values of $\vec{d}_S^{(1)}$ and $\vec{d}_S^{(2)}$ need recalculation as appropriate, for updating.

In the radiation treatment planning system of the present embodiment, as described above, the operator predefines the updating conditions as the conditions for updating $\vec{d}_S^{(1)}$, $\vec{d}_S^{(2)}$, enters the updating conditions from the entry device 502, and sets them in the memory 504 (FIG. 5, step 304).

The radiation treatment planning system determines whether the updating conditions that were set in step 304 of FIG. 5 are satisfied (FIG. 5, step 308) and then if these conditions are satisfied, the system uses the calculated values of the spot irradiation dose $\vec{x}$ and dose matrixes A, B to recalculate and update the objective function (FIG. 5, steps 309, 310). The updating conditions used in step 308 of FIG. 5 are based upon indexes such as an iteration cycle count and variations in objective function value.

As shown in steps 306 to 310 of FIG. 5, the radiation treatment planning system repeats the iterative calculation process while updating $\vec{d}_S^{(1)}$, $\vec{d}_S^{(2)}$ as appropriate, determines whether the ending conditions have been reached (FIG. 5, step 311), ends the iterative calculation upon the ending conditions being satisfied, and ends the search for the spot irradiation dose $\vec{x}$ (FIG. 5, step 312).

Set as the ending conditions for the iterative calculation are, a calculation time, a calculation count, and variations in objective function value.

After the search for the spot irradiation dose $\vec{x}$ in steps 301 to 312 of FIG. 5, the radiation treatment planning system calculates a dose distribution based upon the spot irradiation dose $\vec{x}$ that has been finally derived as a result of the iterative calculation, and displays the calculated dose distribution on the display device 501 (FIG. 3, step 405). If the dose distribution that has been obtained as a result of the iterative calculation is judged by the operator to satisfy the condition specified as the prescription dose, then this condition is defined and under an instruction from the operator, saved in the memory 504 (FIG. 2, steps 204, 205). Conversely if the operator judges the condition not to be satisfied, for example if presence of a region whose dose significantly differs from the prescribed dose is confirmed, there is a need to change the irradiation conditions and set up a new plan (i.e., to execute steps 301 to 312 of FIG. 5 once again).

Figure 6:
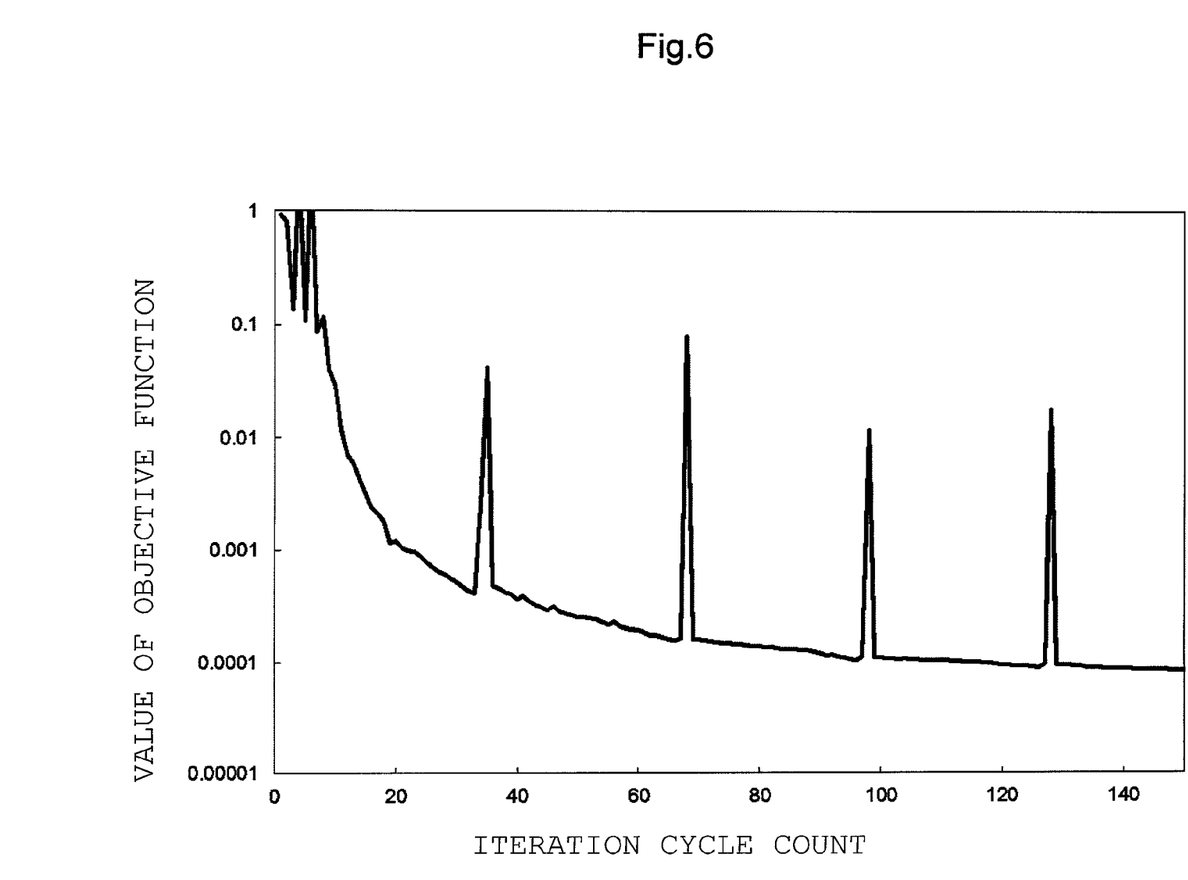
FIG. 6 is a diagram representing a relationship between an optimizing iterative-calculation cycle count and values of an objective function.

The radiation treatment planning system of the present embodiment is configured so that the system can display the value of the objective function during the iterative calculation, that is, the value shown in expression (8). For example, in steps 306 to 310 of FIG. 5, when the system generates the objective function of expression (8) and then repeats the iterative calculation process until the ending condition thereof has been satisfied, the system displays on the display device 501 the value of $F(\vec{x})$ that has been calculated in the iterative calculation process (FIG. 5, step 307). FIG. 6 is a diagram showing an example of displaying the values of the objective function that were calculated in the iterative calculation process.

As shown in FIG. 6, the value of the objective function progressively decreases with increases in iteration cycle count, but after the updating of $\vec{d}_S^{(1)}$, $\vec{d}_S^{(2)}$, the value of the objective function abruptly increases. After this, however, the value of the objective function rapidly decreases and such needle-shaped regions as shown in FIG. 6 are formed. After this, the value of the objective function continues to decrease until $\vec{d}_S^{(1)}$ and $\vec{d}_S^{(2)}$ are updated again, and each time $\vec{d}_S^{(1)}$ and $\vec{d}_S^{(2)}$ are updated, the value of the objective function decreases once again. When the iterative calculation process is thus repeated, the value of the objective function gradually converges.

Next, a description is given below of a more specific example of a way to determine the distance L from the beam axis that becomes the basis for dividing the dose matrixes A, B shown in expression (4), for example.

For example, if a value too small as the distance L is set in expression (4), the element of $A_S$ in expression (4) may not become sufficiently small relative to the element of $A_M$. In this case, if the dose $\vec{d}_S^{(1)}$ calculated using the element of $A_S$ that does not become sufficiently small is handled as a constant, the objective function is likely not to appropriately converge. The distance L from the beam axis must therefore be great enough, compared with the beam size σ (the size of the beam on the surface perpendicular to the traveling direction of the beam).

For example, if the shape of the scanning beam is expressed in a normal distribution, the beam size σ referred to here is a standard deviation.

The beam size σ has its value changing according to the energy of the beam and/or the distance through which the beam travels after entering the patient's body. If the distance L from the beam axis that becomes the basis for division is adopted as a fixed value, therefore, the particular irradiation conditions or specific positions within the target region are likely not to render L appropriate and not to lead to the objective function appropriately converging.

Accordingly in the radiation treatment planning system according to the present embodiment, when the dose matrix A (or B) is divided into $A_M$, $A_S$ (or $B_M$, $B_S$) and generated in step 302 of FIG. 5, a constant multiple of the beam size at each spot, that is, kσ (where "k" is a given constant) is used as the basis for division and the distance L is correspondingly defined. That is to say, L=kσ. When kσ is used as the basis for division, the distance L from the beam axis that becomes the basis for division can be varied according to the particular energy of the beam and the particular relationship between the delivered beam and the calculation points, and thus the dose matrix can be divided into the two components at an appropriate rate.

A more specific example of a way to set up parameter "k" is next described below.

If a small value is set as the value of "k", a time needed to search for the irradiation dose can be shortened. If, however, the value of L, or the value of kσ, is too small as described above, the objective function is likely not to appropriately converge. When the set parameter "k" is used, therefore, whether the objective function can be made to appropriately converge needs to be determined prior to the determination of the irradiation conditions. Use of integral information on the beam shape at positions that neighbor Bragg peaks of the beams of maximum energy and minimum energy used in actual therapy facilitates the determination of whether the objective function can be made to appropriately converge.

More specifically, the beam shape is first integrated over an entire region and a total dose $F_A$ is calculated. After this, the beam shape is integrated within regions of ±kσ (i.e., the beam axis proximal region) from a central position of the beam axis using the set value of "k", and the dose $F_M$ in the beam axis proximal region is calculated. Whether the set parameter "k" can cause the objective function to appropriately converge can be determined from a rate of the calculated dose $F_M$ in the beam axis proximal region to the total dose $F_A$, that is, by whether the rate is equal to or greater than a predetermined ratio. If the convergence is determined to be achievable, the corresponding parameter "k" is used as "k" in the expression of "L=kσ" for calculating the distance L, the basis for the division of the dose matrixes A, B.

As described above, in the present embodiment of the radiation treatment planning system according to the present invention, each dose matrix that is the contribution relating to the doses to the "m" or "n" number of calculation points from the beams delivered to each irradiating position is divided into the dose matrix (beam axis proximal component) $A_M$ or $B_M$ for the points in the target region that are present at distances equal to or less than the distance L from the beam axis of each beam delivered to the particular spot, and the dose matrix (beam axis distant component) $A_S$ or $B_S$ for the points in the target region that are present at distances greater than L from the beam axis of each beam delivered to the particular spot. This division is based upon the respective distances between the beam axis of the beam delivered to the spot, and the plurality of calculation points, and the objective function is set after the division. In addition, when the objective function is set from the operator-defined irradiation conditions and the iterative calculation process is conducted, the dose values $\vec{d}_S^{(1)}$ and $\vec{d}_S^{(2)}$ including the dose matrix components $A_S$, $B_S$ distant with respect to the beam axis are regarded as constants. Thus, even if the beam size increases because of an influence of nuclear reactions in water or scattering inside the irradiation system, this prevents calculation quantities of $\vec{d}_S^{(1)}$ and $\vec{d}_S^{(2)}$ from increasing, suppresses increases in calculation quantity for each step of the iterative calculation process, and reduces the time required for the calculation of the irradiation dose of the beam to the irradiating position.

Additionally, only if previously set updating conditions are determined to be satisfied, in order to allow for the doses $\vec{d}_S^{(1)}$ and $\vec{d}_S^{(2)}$ that the dose matrixes $A_S$, $B_S$, the distant components with respect to the beam axis, impart to the calculation points by use of the irradiation parameter available during the determination, the objective function is recalculated using the values of the dose matrixes A, B and the spot irradiation dose $\vec{x}$ calculated at the particular time, inclusive of the beam axis distant components $A_S$, $B_S$, and the doses $\vec{d}_S^{(1)}$ and $\vec{d}_S^{(2)}$ are correspondingly updated. An influence of the distant components which have been regarded as constants, therefore, can be taken into account and calculation accuracy of the beam irradiation dose can be ensured.

Hence, the treatment planning time required in the present embodiment can be reduced relative to the time required in conventional technology. Furthermore, computation accuracy of the irradiation parameters required for the creation of the therapy plan does not deteriorate, compared with that obtained in the conventional technology.

Moreover, in the radiation treatment planning system of the present embodiment, the parameter $k\sigma$, a constant multiple of the beam size $\sigma$ on the surface perpendicular to the traveling direction of the scanning beam, is used as the basis for dividing the dose matrix A, B into the plurality of $A_M$ and $A_S$ or $B_M$ and $B_S$ components. The use of the parameter $k\sigma$ allows the distance L that becomes the basis for the division, to be varied according to the particular energy level of the beam and the relationship in position between the delivered beam and the calculation points, and thus the dose matrix to be divided into two components at an appropriate rate. These, in turn, allow magnitude of the two components to be changed automatically according to energy level and/or underwater depth, consequently contributing to further speeding up the calculation and to ensuring even higher calculation accuracy.

Besides, radiation treatment planning system of the present embodiment uses the integral information on the shape of the scanning beam to determine "k" in the distance $L=k\sigma$ that is the basis for dividing the dose matrix A, B into the plurality of $A_M$ and $A_S$ or $B_M$ and $B_S$ components, and thereby, before executing the iterative calculation, can predict whether the objective function can be made to appropriate converge. This prediction is beneficial for avoiding an occurrence of a situation under which the objective function might be made incapable of converging, and for further reducing the time needed to calculate the irradiation dose of the beam to the irradiating position.

The present invention is not limited to the above embodiment and can be modified and applied in a variety of other forms.

Scanning irradiation, for example, is broadly divided into two schemes. One is spot scanning, in which, after a defined dose of beam irradiation has been administered to an irradiating position (spot), the beam is turned off once and then after movement of the irradiating position to next one, irradiation is resumed. The other is raster scanning, in which the beam irradiation is continued even during the movement of the irradiating position. The above-described embodiment assumes the spot scanning scheme. Even in the raster scanning scheme, however, determining irradiation conditions requires setting a plurality of irradiating positions in order to perform discrete calculations, so the radiation treatment planning system of the present invention can also be applied to planning out for a treatment that uses the raster scheme.

In addition, although in the above embodiment the dose matrix A, B has been divided into two components, the number of regions into which the dose matrix is divided is not necessarily two.

For example, the dose matrix A, B may be divided into three components. In this case, first, only the component nearest to the beam axis may be regarded as a beam axis proximal component ($A_M$ or $B_M$), and an intermediate component and a distant component are regarded as beam axis distal components ($A_S$, $B_S$), the objective function as shown in expression (8) above may be set, and the iterative calculation may be conducted. Next after the objective function has converged to a certain extent, the component nearest to the beam axis, and the intermediate component may be regarded as the beam axis proximal component ($A_M$ or $B_M$), and only the distant component may be regarded as the beam axis distal component ($A_S$, $B_S$). This may be followed by re-setting of the objective function, and further followed by the execution of the iterative calculation. This method improves a calculation speed during an initial phase of the iterative calculation, while at the same time ensuring even more highly accurate calculation results obtained after the objective function has converged to a certain extent.

Furthermore, while the above embodiment has used a constant multiple of the beam size $\sigma$ as the distance L which is the basis for dividing the dose matrix A into the components $A_M$ and $A_S$ and the dose matrix B into the components $B_M$ and $B_S$, the basis for the division can be any other parameter whose value, as with the beam size, can be varied according to the energy of the delivered beam and the relationship in position between the delivered beam and the calculation points. Examples of any other parameter considered to be useable are full width at half maximum (FWHM) and half width at half maximum (HWHM) measurements of the beam shape. If either the FWHM or HWHM measurement of the beam shape is used, since the distance L from the beam axis that becomes the basis for the division also changes according to the energy of the delivered beam and the relationship in position between the delivered beam and the calculation points, the dose matrix can be divided into two components at the appropriate rate and the calculation can be further speeded up. At the same time, higher calculation accuracy can be obtained. In addition, the operator may previously set up a parameter whose value can be varied according to the energy of the beam and the relationship in position between the beam and the calculation points, and use this parameter as the basis for the division.

What is claimed is:

1. A radiation treatment planning system configured to draw up a treatment plan for conducting a treatment that involves irradiation with radiation, the system comprising:

an entry device for an operator to enter position information about a specific region for which the irradiation with radiation is to be controlled and irradiation conditions thereof;

a storage device for storing the position information about the specific region and the irradiation conditions, each of which has been entered from the entry device; and a calculation unit that sets an objective function based upon the position information and the irradiation conditions stored within the storage device, the calculation unit executing an iterative calculation with respect to the objective function to calculate an irradiation parameter having the smallest value of the objective function;

wherein the calculation unit is operated to:

set a plurality of irradiating positions and a plurality of calculation points within the specific region;

set the objective function by dividing a contribution concerning a dose given to the plurality of calculation points by a beam delivered to each irradiating position into a plurality of components, at least including a beam axis proximal component and a beam axis distant component, in accordance with respective distances between a beam axis of the beam delivered to each irradiation position and the plurality of calculation points; and compute the objective function by, during the iterative calculation, regarding the beam axis distant component included in the plurality of components as a constant, and recalculating, only if previously set updating conditions are determined to be satisfied, the dose to be given to the calculation points, inclusive of the beam axis distant component, by use of an irradiation parameter available upon the determination.

2. The radiation treatment planning system according to claim 1, wherein:

the calculation unit sets up, as a basis for dividing the contribution concerning the dose given to the plurality of calculation points from the beam delivered to each irradiating position into the plurality of components, a parameter whose value is rendered variable according to energy of the delivered beam and a relationship in position between the delivered beam and the calculation points.

3. The radiation treatment planning system according to claim 2, wherein:

the calculation unit determines, from integral information on a shape of the beam, the parameter used as the basis for dividing the contribution concerning the dose given to the plurality of calculation points from the beam delivered to each irradiating position into the plurality of components.

4. The radiation treatment planning system according to claim 1, wherein:

the calculation unit sets up, as a basis for dividing the contribution concerning the dose given to the plurality of calculation points from the beam delivered to each irradiating position into the plurality of components, a value obtained by multiplying by a constant a beam size of the beam on a surface perpendicular to a traveling direction of the beam.

5. The radiation treatment planning system according to claim 4, wherein:

the calculation unit determines, from integral information on a shape of the beam, the parameter used as the basis for dividing the contribution concerning the dose given to the plurality of calculation points from the beam delivered to each irradiating position into the plurality of components.

6. The radiation treatment planning system according to claim 1, wherein:

the calculation unit determines, from integral information on a shape of the beam, the parameter used as the basis for dividing the contribution concerning the dose given to the plurality of calculation points from the beam delivered to each irradiating position into the plurality of components.

* * * * *